United States Patent [19]

Love

[11] Patent Number: 5,980,880
[45] Date of Patent: Nov. 9, 1999

[54] AROMATIC COMPOUND CONTAINING ESSENTIAL OIL AND METHOD OF PRODUCING SAME

[76] Inventor: Marjorie Love, 84 5th Artillery Rd., Fort Leavenworth, Kans. 66027

[21] Appl. No.: 09/015,387

[22] Filed: Jan. 29, 1998

[51] Int. Cl.⁶ ........................................................ A61L 9/00
[52] U.S. Cl. .................... 424/76.1; 424/78.03; 424/78.05
[58] Field of Search ................................ 424/76.1, 78.03, 424/78.05

[56] References Cited

U.S. PATENT DOCUMENTS 4,985,262  1/1991  Camire et al. ........................... 426/302

OTHER PUBLICATIONS

Robert S. Igoe, Food Composition, Dictionary of Food Ingredients, p. 130, 1989.

*Primary Examiner*—S. Mark Clardy
*Assistant Examiner*—Kathryne E. Shelbourne
*Attorney, Agent, or Firm*—Hovey, Williams, Timmons & Collins

[57] ABSTRACT

An aromatic compound containing farinaceous flour, salt, water and at least one essential oil with aroma-giving properties are provided. A carrier oil is preferably provided to lubricate the mixture and blend, dilute and diffuse the essential oil through the compound. The product is made by forming a mixture of ingredients following by heating, cooling, and agglomeration. In use, the aromatic compound can be manually manipulated so that an aroma pleasing to the user emanates from the compound.

15 Claims, No Drawings

AROMATIC COMPOUND CONTAINING ESSENTIAL OIL AND METHOD OF PRODUCING SAME

BACKGROUND OF THE INVENTION

1. Field of the Invention

The present invention relates to the field of aromatherapeutic products. In particular, the present invention is concerned with an aromatic modeling compound containing a mixture of farinaceous flour, salt, water, a carrier oil and at least one essential oil with aroma-giving properties.

2. Description of the Prior Art

The term "aromatherapy" dates to 1928 when it was first used by a chemist in a French perfume company. It traces its roots to ancient civilizations which used aromatic herb and flower oils for healing purposes.

In more modern times, some people have found not only nice smells but also benefits of a therapeutic nature by inhaling particular aromas from scented lotions, soaps, sprays, candles and the like. Most of these aromatherapeutic products are meant to used during bathing, body care, or to scent a particular area of the body. A few of the scents popular for their therapeutic effects are essential oils of lavender, eucalyptus, peppermint and rosemary. While useful at home, the products of the prior art generally cannot be used at work, while traveling, running errands or the like because of bulky packaging, potential spillage, or other problems with portability and versatility. The perceived benefits include a soothing or relaxing effect attributable to the natural characteristics and scents of the products which, in contrast to synthetic fragrances, have the unique ability to penetrate the skin and enter the bloodstream, interacting with the body's own chemistry to promote proper balance of health and well being.

It is also well known to provide self-sustaining or semi-self sustaining compounds which have a putty-like consistency for amusement. Such products include toy compounds sold under the trademarks SILLY PUTTY and PLAY-DOH. Children enjoy the ability to shape these compounds and react well to the colorful appearances, although these products have no perceived smell or certainly none with aromatherapeutic aspects.

I have perceived a need for a product which provides a relaxing and soothing effect through a synergistic combination of tactile and olfactory input, two of the senses less commonly used for information gathering.

There is also a need for a product which is non-tacky and not sticky and can be carried with a person for idle grasping in the hand and which has a pleasing aroma so as not to disturb others.

There is further a need for a product which comforts the user and provides a localized pleasing smell to abate the effect of other less desirable odors.

In addition, there is a need for a product which can be played with in the hands and provides aromatherapy benefits during use; with lingering aromatherapy benefits after use by the transfer of fragrance from an essential oil scent from the product to the user's skin.

SUMMARY OF THE INVENTION

The present invention solves the prior art problems discussed above and provides a distinct advance in the state of the art. In particular, the aromatic compound hereof provides a versatile, portable, and convenient method for receiving the therapeutic benefits of an aromatic product without the difficulties associated with the products of the prior art and with the added benefit of tactile soothing.

The preferred embodiment of the aromatic compound includes a farinaceous flour-based dough impregnated with at least one essential oil. More particularly, the aromatic compound hereof contains from about 30–55% by volume of farinaceous flour and, more preferably, from about 35–45% by volume. For best results, cake flour should be used so as to provide the preferred doughy texture of the compound. In addition to the flour, preferred components of the aromatic compound include salt, water, a carrier oil and at least one essential oil. Preferred salt content ranges are from about 12–30% by volume and, more preferably, from about 15–25%. The preferred salts include table salt, Epsom salts and sea salts. Sea salts, while primarily sodium chloride, also contain some magnesium chloride and other trace elements. Other similar chlorides suitable for use herein include ammonium chloride and potassium chloride. Acceptable substitutes for Epsom salt (magnesium sulfite) may include zinc sulfite and calcium sulfite. A combination of Epsom salts and sea salts in respective quantities is preferred. The amount of water, preferably distilled water, comprises from about 25–45% by volume and, more preferably, 30–40%. At least one essential oil at from about 0–5% by volume and more preferably 0.1–0.5% are included to provide the aroma-giving properties of the compound of the present invention. A carrier oil, as used herein, is derived from vegetable sources and is largely without scent. Such use of a carrier oil provides lubrication to the compound as well as to the user's skin, and acts to blend, dilute and diffuse the essential oil through the compound. While any unperfumed vegetable oil without significant odor may suffice, preferred carrier oils include sweet almond oil and grapeseed oil.

As used herein, essential oil encompasses plant extracts, essences, absolutes, or any other naturally-occurring derivative oil of plants which imparts a fragrance. Essential oils particularly useful and providing aromatherapeutic properties in the present invention include, but are not limited to, oils derived from lavender, eucalyptus, peppermint, rosemary, patchouli, lemon, sweet orange, clary sage, tea tree and ylang ylang.

Other preferred components of the present invention may include starches, potassium bitartrate (cream of tartar), moisturizers, comfrey or other natural colorant, and food coloring. Acceptable starches would include corn starch, wheat starch, rice starch, potato starch, tapioca starch, and peanut starch, with corn starch being most preferred. The moisturizers are preferably fats which are semi-solid at room temperature and most preferably include cocoa butter because of its consistency and moisturizing characteristics. Other vegetable-derived moisturizers suitable in connection with the present invention include corn oil, olive oil, avocado oil, canola oil, caster oil, coconut oil, hazelnut oil, jojoba oil, peanut oil, pecan nut oil, rosehip seed oil, safflower oil, sesame oil, shea butter, and wheat germ oil. Comfrey, an ingredient that provides coloring properties to yield cosmetic elegance to the compound, is preferred in the form of unadulterated comfrey root powder. Food coloring, if used, is preferably selected from naturally dried, FDA approved food colorants to yield the compound of the desired color and tone.

The preferred method of producing the aromatic compound of the invention includes the steps of first forming a mixture including therein from about 30–55% by volume farinaceous flour with 12–30% by volume salt. Next, water is added to the mixture in quantities from about 25–45% by volume in conjunction with 0–5% of a carrier oil and 0–5% of at least one essential oil. The combined mixture is heated again over a medium flame while stirring until the mixture thickens and agglomerates. The agglomerated product is then cooled to form the aromatic compound of the present invention.

The user manually manipulates the aromatic compound hereof which emanates an aroma associated with the essential oil or oils chosen by the user to be pleasing. Additionally, the aromatic compound exudes some of the aroma-giving oil and carrier oil for sorption onto the skin of user thereby providing a moisturizing benefit. In addition, the manipulation by the user is tactilely pleasant and soothing, so that by forming, holding and squeezing the compound, the user enjoys the tactile sensation as well as the aromatherapy effects.

DETAILED DESCRIPTION OF THE PREFERRED EMBODIMENT

The following examples describe the formation of the aromatic compound in accordance with the present invention. It is to be understood that these examples are presented by way of illustration only, and nothing therein should be taken as a limitation upon the overall scope of the invention.

In each example, the following broad and preferred ranges of ingredient content are used in the production of the aromatic compound of the present invention:

TABLE 1

| INGREDIENT | BROAD RANGE | PREFERRED RANGE |
| --- | --- | --- |
| Farinaceous Flour | 30–55% b.v. | 35–45% b.v. |
| Salt | 12–30% b.v. | 15–25% b.v. |
| Water | 25–45% b.v. | 30–40% b.v. |
| Starch | 0–5% b.v. | 2–3% b.v. |
| Cream of Tartar | 0–4% b.v. | 1–2% b.v. |
| Comfrey | 0–3% b.v. | 0.1–0.9% b.v. |
| Moisturizer | 0–3% b.v. | 0.1–0.9% b.v. |
| Carrier Oil | 0–3% b.v. | 0.1–0.9% b.v. |
| Essential Oil | 0–5% b.v. | 0.1–0.5% b.v. |

EXAMPLE 1

In this example, an aromatic compound was prepared in accordance with the present invention. The ingredients are set forth below:

TABLE 2

| INGREDIENT | FLUID OUNCES | % BY VOLUME |
| --- | --- | --- |
| Cake Flour | 10 | 42.77 |
| Ground Epsom Salt | 2 | 8.55 |
| Ground Sea Salt | 2 | 8.55 |
| Cornstarch | 0.5 | 2.14 |
| Cream of Tartar | 0.33 | 1.41 |
| Comfrey Root Powder | 0.17 | 0.73 |
| Distilled Water | 8 | 34.22 |
| Melted Cocoa Butter | 0.17 | 0.73 |
| Sweet Almond Oil | 0.17 | 0.73 |
| Lavender Oil (Essential Oil) | 0.04 | 0.17 |

First, the cake flour, Epsom salt, sea salt, cornstarch, cream of tartar and comfrey root powder were admixed in a common container. Next, the water, cocoa butter, sweet almond oil, and lavender oil were added to the original mixture and heated over a medium flame for approximately three minutes until the combined mixture thickened and agglomerated. The mixture was then removed from heat. After the aromatic compound cooled to ambient temperature, the user manually manipulated the product and inhaled the aroma of the essential oil of lavender in addition to absorbing the moisturizing oil into the skin of the hands.

EXAMPLE 2

In this example, another preferred embodiment of the present invention was prepared. The ingredients are set forth below:

TABLE 3

| INGREDIENT | FLUID OUNCES | % BY VOLUME |
| --- | --- | --- |
| Cake Flour | 10 | 42.70 |
| Ground Epsom Salt | 2 | 8.54 |
| Ground Sea Salt | 2 | 8.54 |
| Cornstarch | 0.5 | 2.13 |
| Cream of Tartar | 0.33 | 1.41 |
| Comfrey Root Powder | 0.17 | 0.73 |
| Distilled Water | 8 | 34.12 |
| Melted Cocoa Butter | 0.17 | 0.73 |
| Sweet Almond Oil | 0.17 | 0.73 |
| Eucalyptus Oil (Essential Oil) | 0.04 | 0.17 |
| Peppermint Oil (Essential Oil) | 0.04 | 0.17 |

First, the cake flour, Epsom salt, sea salt, cornstarch, cream of tartar and comfrey root powder were admixed in a common container. Next, the water, cocoa butter, sweet almond oil, eucalyptus oil, and peppermint oil were added to the original mixture and heated over a medium flame for approximately three minutes until the combined mixture thickened and agglomerated. The mixture was then removed from heat. After the aromatic compound cooled to ambient temperature, the user manually manipulated the product and inhaled the aroma of the essential oils of eucalyptus and peppermint in addition to absorbing the moisturizing oil into the skin of the hands.

I claim:

1. In a malleable, agglomerated dough compound including respective quantities of the ingredients of farinaceous flour, salt, and water, the improvement which comprises an aroma-giving component mixed into said compound ingredients, said aroma-giving component including an essential oil, and said compound, upon manual manipulation thereof, exuding some of said aroma-giving component for sorption of the latter onto the skin, the amount of flour present in said compound being greater than the amount of said essential oil, said salt being present at a level of from about 12–30% by volume.

2. The compound of claim 1, said farinaceous flour comprising cake flour.

3. The compound of claim 1, said salt selected from the group consisting of table salt, sea salt, Epsom salt, and mixtures thereof.

4. The compound of claim 1, said water comprising distilled water.

5. The compound of claim 1, said compound further including a respective quantity of a non-perfumed vegetable-derived carrier oil.

6. The compound of claim 1, said compound further including a respective quantity of potassium bitartrate.

7. The compound of claim 1, said compound further including respective amounts of starch and comfrey.

8. The compound of claim 7, said comfrey comprising comfrey root powder.

9. The compound of claim 1, said compound further including a respective quantity of cocoa butter.

10. The compound of claim 1, said compound including from at least 30–55% by volume farinaceous flour.

11. The compound of claim 1, said compound including from about 25–45% by volume water.

12. The compound of claim 1, said compound including up to 2% by volume of at least one essential oil.

13. The compound of claim 1, said compound including up to about 3% by volume of at least one carrier oil.

14. A method for forming an aroma-giving malleable agglomerated dough compound comprising the steps of:

admixing respective quantities of farinaceous flour and salt;

adding liquid fractions of water, a carrier oil and at least one essential oil, the amount of said flour being greater than the amount of said essential oil, said salt being present at a level of from about 12–30% by volume;

heating the combined mixture over a medium flame;

stirring the mixture; and cooling said mixture to ambient temperature until said mixture thickens and agglomerates into said agglomerated dough.

15. A method of forming an aroma-giving, malleable compound according to claim 14, including the steps of adding respective quantities of potassium bitartrate and comfrey and mixing with said farinaceous flour and salt prior to the addition of said liquid fractions.

\* \* \* \* \*